United States Patent [19]

Page et al.

[11] Patent Number: 4,559,229

[45] Date of Patent: Dec. 17, 1985

[54] AVIAN PROVENTRICULITIS VACCINE

[75] Inventors: Robert K. Page, Winder; Pedro Villegas, Athens; Caswell S. Eidson, Athens; Daniel Gaudry, Athens, all of Ga.

[73] Assignee: Research Foundation, Athens, Ga.

[21] Appl. No.: 400,024

[22] Filed: Jul. 20, 1982

[51] Int. Cl.$^4$ ................ A61K 39/12; C12N 7/00
[52] U.S. Cl. ........................... 424/89; 435/235
[58] Field of Search ............... 424/88, 89; 435/235

[56] References Cited

U.S. PATENT DOCUMENTS

| | | | |
|---|---|---|---|
| 2,998,349 | 8/1961 | Peterson et al. | 424/89 |
| 3,534,136 | 10/1970 | Dunlop | 424/89 |
| 3,629,396 | 12/1971 | Yates et al. | 424/89 |
| 4,196,265 | 4/1980 | Koprowski et al. | 435/2 |
| 4,302,444 | 11/1981 | Baxendale | 424/89 |
| 4,444,293 | 5/1969 | Hudson | 424/89 |

FOREIGN PATENT DOCUMENTS

| | | | |
|---|---|---|---|
| 7904021 | 4/1980 | Netherlands | 424/89 |

OTHER PUBLICATIONS

Jackson et al., Aust. Vet. J., Sep. 1977, 53(9), pp. 457–459.

"Microbiology, Including Immunology & Molecular Genetics", 3rd Edition by Davis et al, pp. 1206–1212.

*Primary Examiner*—Sidney Marantz
*Assistant Examiner*—Shawn P. Foley
*Attorney, Agent, or Firm*—Oblon, Fisher, Spivak, McClelland & Maier

[57] ABSTRACT

A process of preparing a vaccine capable of protecting poultry against avian proventriculitis which comprises: separating proventriculitis reovirus from reovirus-carrying tissue of a poultry animal diseased with proventriculitis; inoculating a cell culture capable of sustaining the growth and replication of the reovirus; extracting the virus from cellular and nonviral components, and rendering the reovirus into a form suitable for administration to poultry, yields a vaccine and an immunization method.

12 Claims, No Drawings

AVIAN PROVENTRICULITIS VACCINE

BACKGROUND OF THE INVENTION

1. Field of the Invention

The present invention relates to the isolation of the etiologic agent of avian proventriculitis, its identification as a reovirus and the preparation of a vaccine against the disease.

2. Brief Description of the Prior Art

A clinical syndrome in chickens characterized by stunted growth, poor feathering and an increase in leg weakness has been described (Kouwenhoven, V. et al, Vet. Sci. Com., 2:253-259 (1978)). In affected flocks 5-20% of the chicks exhibit growth retardation by one week of age; an increase in lameness and very poor feather development is apparent by two weeks of age. The most prevalent clinical lesions are an enlargement of the proventriculus with areas of necrosis, hemorrhage, and catarrhal enteritis (Kouwenhoven, V. et al, Avian Pathology, 7:183-187 (1978)). Studies indicate that the syndrome can be reproduced in susceptible one-day-old chicks by direct contact with infected chickens or by the injection of homogenized intestinal tracts from infected chickens (Vertommen, N. et al, Ibid, 9:133-142 (1980)). Biochemical examination of plasma from these chicks indicate a low plasma carotenoid level and an increase in alkaline phosphatase activity.

A number of cases with similar clinical lesions have been seen in all of the major broiler growing areas of the southeastern United States. The problem is highly farm-related and is especially severe on large farms and on farms where brooding and growing are conducted simultaneously. The first clinical signs occur when the chicks are about two weeks of age. The chicks appear chilled and do not consume as much feed as expected; the growth rate is retarded with undigested feed passed in the droppings. Many of the droppings are covered with an orange exudate, frequently leading to a misdiagnosis of coccidiosis. At about three weeks of age, paleness of the shank and very poor feathering are commonly seen. The clinical manifestations of this problem and the lesion patterns are extremely variable, making diagnosis of the syndrome difficult.

Post mortem lesions, like the clinical signs, present a confusing picture for the diagnostician. The lesions are not consistent from bird to bird; however, the lesions seen most consistently include an enlarged proventriculus or an engorgement of the glands in the proventriculus. In several instances, there will be a necrosis of the proventricular glands and a small atonic gizzard. Hyperemia and hemorrhages are frequently seen in the duodenal area, and the lower portion of the GI tract will be ballooned and very friable. Perosis and femoral head necrosis are found in many of the chickens exhibiting the aforementioned lesions, and encephalomalacia is also frequently found.

The disease has been given several different names: malabsorption syndrome, pale bird syndrome, brittle bone disease, helicopter disease, and proventriculitis. The latter ("proventriculitis") will be used throughout the present specification and claims.

In order to further understand the nature and scope of the present invention, it is also worth describing the nature of the so-called "reoviruses". The term "reovirus" (Respiratory Enteric Orphan Virus) refers to a group of RNA viruses that infect both the respiratory and intestinal tracts, usually without producing disease (See for example, Davis, B. D. et al, "Microbiology. Including Immunology and Molecular Genetics," 3rd edition, (1980) Harper & Rowe Publishers, Hagerstown, pp. 1206-1212). They include species that infect humans, birds, dogs and monkeys. They appear to be ubiquitous in nature, since specific viral inhibitors (presumably antibodies) have been found in the serum of all mammals tested except the whale. Humans and many other species, (including cattle, mice and monkeys) are naturally susceptible to reoviruses.

Reoviruses have frequently been isolated from the feces and respiratory regions of healthy persons, as well as from patients with a variety of clinical illnesses, particularly minor upper respiratory and gastrointestinal disease. The relation of these viruses to disease is not clear. In fact, Davis et al, supra, at page 1212, state:

The reovirus infections do not seem to be of great clinical importance, and further studies are needed to define their pathogenic potential. Both the respiratory and the gastrointestinal tracts may well be sources for their spread . . . . Antibodies are also frequently found in various wild and domestic animals, but it is not known whether the animals serve as reservoirs for human infections.

Since the meager data assign a limited pathogenicity to these viruses, specific immunization procedures are not warranted.

This statement, coming in 1980, reflects the belief in the art that reoviruses are not involved in any serious diseases or that, at best, significant research would have to be carried out in order to define their pathogenic potential.

A need, therefore, continues to exist for the identification of the etiologic agent of avian proventriculitis, as well as its isolation and possible preparation of a vaccine against the disease.

SUMMARY OF THE INVENTION

It is therefore an object of the invention to provide a method for the purificaion for, and a purified form of the etiologic agent of avian proventriculitis.

It is another object of the invention to provide an avian proventriculitis vaccine.

It is still another object of the invention to provide a method of protecting poultry against proventriculitis.

These and other objects of the invention which will hereinafter become more readily apparent, have been attained by providing:

A vaccine capable of protecting poultry against proventriculitis.

These objects have also been attained by providing a substantially pure form of avian proventriculitis reovirus.

BRIEF DESCRIPTION OF THE PREFERRED EMBODIMENTS

The present invention is based on the discovery that the etiologic agent for avian proventriculitis is a reovirus. Following this discovery, it is now possible to isolate and purify this agent, and prepare appropriate vaccines based on attenuated or unattenuated or inactivated forms of the reovirus.

The discovery that the agent is a reovirus came as a surprise, since it comes in the context of the belief in the art, presented by Davis et al, supra, that "reovirus infections [do] not seem to be of great clinical importance". Also, the preparation of a proventriculitis vaccine based on such reovirus stands in sharp contrast to the same Davis et al statement quoted previously to the effect that, given the limited pathogenicity of the reoviruses "specific immunization procedures are not warranted".

The discovery of the reovirus and the preparation of a vaccine against the disease opens the possibility of protecting poultry by wide-range immunization procedures, greatly affecting the economics of the poultry industry.

The proventriculitis virus can be isolated from the intestinal tract and visceral organs of poultry (e.g., chickens, turkeys, ducks, etc.) showing clinical signs of proventriculitis.

Tissue homogenates from visceral organs and intestinal content can be processed by grinding each sample in sterile growth medium, appropriate for the growth of the derived animal cells, but containing appropriate antibiotics such as penicillin, streptomycin or gentamycin, in order to prevent bacterial contamination. Grinding is carried out for a time and under conditions sufficient to allow the extraction of virus particles into the growth medium. Samples are then normally filtered through a filter capable of allowing passage of the virus therethrough but not of any cells or aggregates thereof.

The filtrate is normally inoculated into confluent monolayers of pathogen-free cells capable of sustaining the growth of viruses and the replication and culture thereof. Such cells include chicken embryo kidney cells, and chicken embryo fibroblasts. The supernatant can also be inoculated in 9–11 day-old chicken embryos. The cells are grown in an appropriate growth medium, which normally contains fetal calf serum. The cells in monolayer culture are observed daily until the activity of the virus upon the cells is found. If the effect is not observed in three to five days, the plates can be frozen for three times and further passaged. At least four blind passages should be made before a sample is to be considered negative.

In samples where cytopathic effects are observed, infected cell plates are frozen a few times and cell culture fluid centrifuged under g conditions and times sufficient to separate cell fragments from viral particles, e.g., at $5,000 \times g$ for 20 minutes. The supernatant which contains the virus is then ultracentrifuged under g conditions and times sufficient to precipitate the viral particles, e.g., at $110,000 \times g$ for 45 minutes on an ultracentrifue. The resulting pellet is resuspended in physiologically buffered solution, and contains the active virus.

The isolates can be identified as reoviruses on the basis of their cytopathogenicity, insensitivity to treatment with chloroform, presence of RNA, and in some cases, electron microscopy. Most isolates can be obtained after 2–3 blind passages in chicken embryo cells.

Electron microscopy reveals that the viral isolates are 68–72 nm in diameter, and icosohedrons with a double capsid shell. All of the isolates are insensitive to both chloroform and IUDR (iododeoxyuridine), indicating that they are nonenveloped and of RNA type nucleic acids respectively. The viral strains are heat stable for up to 6 hours at 56° C. and they do not hemagglutinate red blood cells (RBC's).

Innoculation of chicken embryos with active viral strains produces mortality within 1–7 days. Macroscopic lesions include thickening and necrosis of the chorioallantoic membrane, liver necrosis and hemorrhagic embryos. Microscopically, chorioallantoic membranes become inflamed, necrotic and undergo fibroblastic proliferation. Large basophilic granula inclusions are also found in fibroblast type cells of the chorioallantoic membrane in embryos innoculated with certain strains.

The availability of purified isolated avian proventriculitis virus, substantially free of cellular components and other nonviral components, allows for the preparation of proventriculitis vaccine. The vaccine can be prepared according to a number of well-known methods in the art. Thus, a vaccine can be prepared from the whole live virus or from immunologically active but nonpathogenic subcomponents thereof, such as capsids and the like obtained by splitting with enzymes or solvents. Chemically attenuated live or killed viral vaccines can also be used, for example by the treatment of virus with propiolactone, dilute formalin, ethyleneimine, halogenated hydrocarbons, and the like. These agents decrease virus pathogenicity while allowing the material to retain immunogenicity.

Another technique for attenuating the virulence of the virus is to develop avirulent or slow growing strains, or mutants incapable of sustained replication in the host. This is generally known in the art as "genetic attenuation" and can be done by genetic manipulations or by serial passages. For example, the production of live attenuated viruses can be carried out by adapting the isolated virus to cultures containing avian tissue cells and attenuation for example by 10–200 passages in such cultures, after which said viruses multiply and a vaccine is then prepared. Another method of producing live vaccine is to select and culture clones. If the infected cells are used for the production of a live vaccine, it is advantageous to release the virus from the cells. Techniques for preparing vaccines are generally detailed in a publication such as "Newcastle Disease Vaccines: Their Production and Use"—Allan, W. H., J. E. Lancaster and B. Toth; Food and Agricultural Organization, Rome 1978. This text is herein incorporated by reference.

The vaccines, whether live or attenuated, in their many different forms can be prepared in suspension in a manner known per se with a pharmacologically acceptable vaccine carrier, such as a bioacceptable oil. It is advantageous to add thereto a stabilizer, particularly if a dry preparation is prepared by lyophilization. An adjuvant such as aluminum hydroxide may also be added. The stabilizing agent can be a carbohydrate such as sorbitol, mannitol, starch, sucrose, dextran or glucose; a protein like albumin or casein; a protein containing agent like bovine serum, or skimmed milk, and a buffer such as alkaline metal phosphate.

The vaccine can be administered to poultry to prevent the same from developing proventriculitis. The poultry includes chickens, turkeys, ducks, hens, and roosters.

Immunization can occur anywhere between the time of birth to approximately 5 to 7 weeks. This will allow for the vaccine to provide adequate protection in broiler chickens which are the more severely affected by the condition. However, immunity could last longer than these periods.

The vaccine can be administered, for example, by forced oral administration to individual chickens, wherein a few birds of a flock receive the vaccine and the remaining birds become vaccinated by infection. Another method is to administer the vaccine in the drinking water, by wing stabbing methods, subcutaneously, intramuscularly, by the nasal or eye drop route, etc. Most preferably, the vaccine is administered to reproductive hens, so as to provide immunity to the progeny.

A dosage of anywhere between $5 \times 10^6$ viral particles to $1.5 \times 10^7$ viral particles per administration is suitable, most preferred about $10^7$ virus particles per administration.

The present methods for preparing the vaccine lead to titers of anywhere between $10^7$ to $10^{8.5}$. It is, however, envisioned that the titer can be increased by concentration or by technical improvements in the methodology.

The availability of purified proventriculitis reovirus also allows for the development of immunoassay procedures for the detection of the disease in its early stages. Antibodies (IgG, IgM) against the reovirus can be generated in appropriate animals (poultry, horses, rabbits, goats, and the like), or in hybridomas (see e.g. Koprowski et al, U.S. Pat. No. 4,196,265, or Wands et al, U.S. Pat. No. 4,271,145 which are herein incorporated by the reference). These antibodies can be used in any of the multiple immunoassay procedures currently available (see, for example T. Chard "An Introduction to Radioimmunoassay and Related Techniques", North-Holland, 1978, or Schuurs, A. H. W. M. et al, "Enzyme Immunoassay", Clin. Chim. Acta 81, 1–40 (1977), both of which are herein incorporated by reference). For example, the presence of the reovirus in poultry samples can be detected by radioimmunoassay, enzyme immunoassay, or latex agglutination immunoassay, in physiological samples of poultry such as blood, droppings, tissue and the like. The technique utilized can be e.g. competitive, "sandwich" (forward, reverse or simultaneous), double antibody, or enzyme cascade, all which are all well known to those skilled in the art. It may be useful for certain techniques to prepare, by art-known methods, detectably labeled proventriculitis reovirus, such as reovirus labeled with a radiolabel ($I^{125}$, $C^{14}$, $H^3$, $P^{32}$ etc.), with an enzyme (alkaline phosphatase, peroxidase, etc.), with a fluorescent probe, and the like. The antibodies can be either in solution or immobilized, such as, for example, on the inside of tubes, on polymer or glass beads, on plastic strips, and the like.

Having now generally described this invention, the same will become more readily apparent by reference to certain specific examples which are included herein for purposes of illustration only and are not intended to be limiting of the invention or any embodiment thereof.

EXAMPLE 1

Identification and Serological Differentiation of Several Viral Strains Isolated From Chickens with Proventriculitis

Materials and Methods

Source. Viral strains were isolated from the intestines from 3- to 6-week-old broilers exhibiting clinical signs of proventriculitis.

Procedures Used for Virus Isolation. Tissue samples were processed by grinding each sample in 15 ml sterile tryptose phosphate broth containing 100 units of penicillin and 100 micrograms of streptomycin per milliliter. The samples were then filtered through a 0.45 micron filter and innoculated onto confluent monolayers of specific pathogen-free (SPF) chicken embryo kidney cells (CEKC). Innoculated and uninnoculated CEKC monolayers were observed daily for cytopathic effect. If the effect was not observed in 3 to 5 days, the plates were frozen-thawed three times and further passaged. At least four blind passages were made before a sample was considered negative.

Electron microscopy. Briefly, for sample preparation, the infected CEKC plates were frozen-thawed three times and cell culture fluid was centrifuged at 5,000×g for 20 minutes. This supernatant was then ultracentrifuged at 110,000×g for 45 minutes on a Beckman ultracentrifuge (Model L2-65B). The resulting pellet was resuspended in 0.1 ml of sterile phosphate buffered saline and 1 drop was allowed to dry on a coated grid. The sample was then negatively stained with 2% phosphotungstic acid pH 7.2 for 1 minute and observed with a transmission electron microscope.

Chloroform Sensitivity. The method described by Rovozzo and Burke (A Manual of Basic Virological Techniques. Prentice Hall, Inc. Englewood Cliffs, N.J., 1973) was followed, except that one aliquot of the virus suspension was treated with 10% reagent grade chloroform, the other aliquot was left untreated and the tubes were centrifuged at 1,000 g for 20 minutes. Known chloroform sensitive and resistant viruses were always processed simultaneously in the same manner.

Iododeoxyuridine (IUDR) Inhibition and Heat Stability. IUDR inhibition and heat stabiity were determined following the procedure of Rovozzo and Burke, supra, utilizing CEKC as the indicator system.

Hemagglutination tests. Virus infected CEKC monolayers showing 80% citopathic effect were frozen thawed three times and one drop of the supernatant was mixed on a clean white ceramic plate with an equal amount of 5% chicken red blood cells. The plate was gently rocked for one minute and observed for the presence of hemagglutination. Chicken red blood cells and positive controls were also run in the same manner.

Pathogenicity in Embryos. SPF chicken embryos were inoculated with four of the viral isolates (approximately $10^6$ PFU/embryo) by the chlorioallantoic sac (CAS), chorioallantoic membrane (CAM), and yolk sac (YS) routes (5 embryos/route/viral isolate). Records on mortality, macroscopic and microscopic lesions were noted.

Replication Cycle. The one-step growth curve was determined for one of the viral strains (81-5) following the procedure described by Rovozzo and Burke, supra, except that the inoculum used was sufficient so that every cell in the culture was infected ($10^5$ $TCID_{50}$/plate), and the sample time was decreased to two hour intervals for a total of twenty-one hours. Chicken embryo fibroblasts were used to titrate the intracellular and extracellular virus in microtiter plates (5 wells/dilution).

Cross Neutralization Studies. The beta neutralization method with a constant amount of virus and variable amount of serum was employed for all cross neutralization studies. The tests were performed in sterile flat bottom microtiter plates using SPF CEKC as the indicator system. Cell and virus controls as well as known positive (homologous) and negative (SPF) sera were included in every test. The technique consisted of adding in the first row of a microtiter plate 100 microliters of a virus dilution containing 20 plaque forming units (PFU). Rows 2–11 received 50 microliters/well of diluted virus. The twelfth row was blanked with 50 microliters/well Hanks Balanced Salt Solutions (HBSS) and served as the cell control. Twenty-five microliters of each serum sample was mixed with the 100 microliters in the wells of the first row. After discarding 25 microliters of the mixture, the serum was serially diluted by passing 50 microliters. The eleventh row was left as a virus control. The plates were incubated at 37° C. for forty-five minutes and then approximately $2 \times 10^5$ CEKC were added to each well. After incubation at 37° C. in 5% $CO_2$ for 3-4 days the plates were fixed with 95% ethanol and stained with 1% crystal violet. The titer of the serum was read as the reciprocal of the highest dilution which inhibited clearing of the monolayer. Serum samples were always run in triplicate and were repeated several times.

Production of Antisera. Several three to four week old SPF chickens, which were reared in Horsfall isolation units, were inoculated intraocular, intranasal and orally with approximately $10^6$ PFU in 0.2 ml of cell and serum-free live virus. Two weeks later they were reinfected by the same route with 0.25 ml of the same virus preparation. Blood was collected two weeks after that, centrifuged at 200 g for 10 minutes and the serum was collected and stored in 2-3 ml aliquots at $-70°$ C.

Calculation of relatedness values. Relatedness values (R) were calculated using the formula of Archetti and Horstfall ("Persistent Antigenic Variation of Influenza A Viruses After Incomplete Neutralization in Ovo with Heterologous Immune Serum." J. of Exp. Med. 92: 441–462. 1950. The resulting R values were evaluated (Table 1) based on the work of Brooksby ("Variants and Immunity: Definitions for Serological Investigations. In: International Symposium on Foot and Mouth Disease Variants and Immunity". Lyon, France. Symposium Series Immunobiology, 1967) which interprets the R values as shown in Table 1.

TABLE 1

| Interpretation of relatedness values. | |
|---|---|
| R value (%) | Interpretation |
| 0–10 | Serotype |
| 10–32 | Major subtype |
| 32–70 | Minor subtype |
| >70 | Little or no |

Results

For virus isolation, two or three blind passages were usually necessary before CPE was observed, although in some cases CPE was detected in the first passage. As early as 1-2 days post-inoculation there was syncytial formation which developed into multinucleated giant cells. By 3-5 days post-inoculation large areas of the monolayer had detached.

As seen in Table 2, the electron microscopy results revealed that the viral isolates were 68–72 nm in diameter, with icosahedral symmetry and with a double capsid shell. All of the isolates were insensitive to both chloroform and IUDR indicating that they were non-enveloped and of RNA type nucleic acid, respectively. The viral strains were heat stable for up to six hours at 56° C. and they did not hemagglutinate chicken RBC's.

TABLE 2

| Characteristics of viral strains isolated from chickens with Proventriculitis. | | | | | | |
|---|---|---|---|---|---|---|
| Character- | Viral Strains | | | | | |
| istics | $CO_8$ | 43A | 81-5 | 45 | 82-9 | 197#28 |
| Electron microscopy | | | | | | |
| diameter (nm) | 72 | 68–70 | 72 | 70 | 72 | 72 |
| icosahedron symmetry | Yes | Yes | Yes | Yes | Yes | Yes |
| double capsid shell | Yes | Yes | Yes | Yes | Yes | Yes |
| Presence of envelope | No | No | No | No | No | No |
| Nucleic acid type | RNA | RNA | RNA | RNA | N.D.[a] | N.D. |
| Heat stability[b] | Yes | Yes | Yes | Yes | N.D. | N.D. |
| Hemagglu- tination of chicken RBC's | No | No | No | No | No | No |

[a] N.D. = not done.
[b] Six hours at 56° C.

Table 3 shows the results of the inoculation of chicken embryos with four of the viral strains. Regardless of the route of inoculation, mortality was observed between one to seven days post inoculation. Embryos inoculated with strains $CO_8$ and 81-5 died between 3-7 days post inoculation while those embryos inoculated with strains 43A and 45 dies within 3 days after inoculation.

Macroscopic lesions included thickening and necrosis of the chorioallantoic membrane, liver necrosis and hemorrhagic embryos. Microscopically the CAM were inflamed, necrotic and undergoing fibroblastic proliferation. Large, basophilic, granular inclusions were also found in fibroblast type cells of the CAM in embryos inoculated with strain 43A. Strain $CO_8$ produced necrosis, proliferating fibroblasts and giant cells in the liver, and also hyperplasia of the epithelial cells of the proventriculus.

TABLE 3

| Mortality of chicken embryos after inoculation with sevaral viral strains by three different routes. | | | | |
|---|---|---|---|---|
| Viral strain | Titer of inoculum PFU/0.1 ml | Route of inoculation[a] | | |
| | | CAS | CAM | Y.S. |
| | | Days till embryo death | | |
| $CO_8$ | $10^6$ | 6-7 | 4-6 | 3-4 |
| 81-5 | $10^{5.4}$ | 6 | 4 | 5 |
| 43A | $10^{5.4}$ | 2-3 | 2 | 3[b] |
| 45 | $10^{5.5}$ | 1-3 | 2 | 3[c] |

[a] CAS = choriallantoic sac.
[b] Inoculum = $10^{4.4}$ PFU/0.1 ml.
[c] Inoculum = $10^{4.5}$ PFU/0.1 ml.

The results of the one step growth curve for strain 81-5 are shown in Table 4. It was found that during the first 5 hours after inoculation there was no significant rise in virus titer over the original inoculum titer. Therefore, the original inoculum titer was considered base line. Between 5 and 7.5 hours there was a substantial increase in the intracellular virus titer while the extracellular titer remained below base level. Total virus increased rapidly between 5 to 10 hours and continued increasing at a much slower rate after that. At 7.5 hours the extracellular virus titer started to rise rapidly and continued to gradually increase after 10 hours. By 21 hours the intracellular and total virus titers had dropped slightly.

TABLE 4

Titer of the intracellular, extracellular and total virus obtained periodically for the determination of the one step growth curve for strain 81-5

| Virus | Hours post inoculation | | | | | | |
|---|---|---|---|---|---|---|---|
| | 0 | 2 | 3.5 | 5 | 7.5 | 10 | 21 |
| Extracellular | $10^{3.6}$ | $10^{4.9}$ | $10^{4.9}$ | $10^{4.2}$ | $10^{4.4}$ | $10^{6.4}$ | $10^{2.4}$ |
| Intracellular | $10^{4.8}$ | $10^{4.9}$ | $10^{5.2}$ | $10^{5.4}$ | $10^{9.3}$ | $10^{9.6}$ | $10^{9.1}$ |
| Total | $10^{4.8}$ | $10^{5.2}$ | $10^{5.4}$ | $10^{5.4}$ | $10^{9.3}$ | $10^{9.6}$ | $10^{9.2}$ |

$TCID_{50}/ml$.

Geometric mean cross neutralization titers obtained with homologous and heterologous antisera are presented in Table 5. Strains 43A, 45, 81-5 and S1133 had a very low neutralization titer with the $CO_8$ antiserum while the homologous and heterologous titers were always of much higher values. Strain $CO_8$ had a very low neutralizating activity against antisera from strains 43A and 81-5 while against antisera from strain 45 and S1133 the neutralization titers were higher.

TABLE 5

Geometric mean cross neutralization titers between several viral strains.

| Antigen | Antisera | | | | |
|---|---|---|---|---|---|
| | 43A | 45 | $CO_8$ | 82-5 | S1133 |
| 43A | 603 | 757 | 37 | 905 | 1106 |
| 45 | 1490 | 1120 | 50 | — | 1955 |
| $CO_8$ | 40 | 474 | 269 | 70 | 190 |
| 81-5 | 326 | 711 | 9 | 577 | 1902 |
| S1133 | 508 | 1920 | 22 | 422 | 905 |

Relatedness values obtained for all strains are presented in Table 6. It was found that isolate $CO_8$ had an R value of 6.19 and 6.07 for strains 43A and 81-5, respectively. These values were interpreted as serologically differenc types. The r values for strain $CO_8$ compared with strains S1133 and 45 were 12.49 and 19.58, respectively. These values were interpreted as major subtype differences. Little or no difference was found when strain S1133 was compared with strains 43A, 81-5, and 45. No difference was found among these last 3 strains.

TABLE 6

Relatedness values of several reovirus strains.

| Strains | R value (%) | Interpretation |
|---|---|---|
| $CO_8$ + 43 | 6.19 | Serotype |
| $CO_8$ + 81-5 | 6.07 | Serotype |
| $CO_8$ + S1133 | 12.49 | Major subtype |
| $CO_8$ + 45 | 19.58 | Major subtype |
| S1133 + 43A | 101.44 | Little or no |
| S1133 + 81-5 | 124.00 | Little or no |
| S1133 + 45 | 192.42 | Little or no |
| 81-5 + 43A | 92.12 | Little or no |
| 43A + 45 | 143.95 | Little or no |

Discussion

Viruses were not isolated from all intestinal samples processed. The physiochemical and morphological characteristics of the viruses isolated indicate that they belong to the reoviridae family.

Cross-neutralization studies indicate that the reovirus isolates belong to, at least, two different serotypes. Strain $CO_8$ has a serotype or major subtype difference when compared with the other reovirus strains including reovirus S1133. Broilers given viral arthritis vaccine (S1133) may not be protected against infection with viral strains similar to isolate $CO_8$.

EXAMPLE 2

Reproduction of Proventriculitis with Virus Isolates in Broiler Chickens

Materials and Methods

All of the trials reported herein were conducted on broiler chicks obtained from a breeder flock with a viral arthritis serum neutralization titer of 15. Proventriculitis had been seen in several farms that contained progeny from this flock. In trial 1 sixty chickens were divided into six groups of ten chicks each. Two groups each were injected at one day of age with isolate one or two and two groups were noninjected controls. In trial 2 seventy chicks were divided into seven groups of ten chicks. Six groups were injected at one day of age with isolates obtained from several different farms and one group was a noninjected control. All of the birds were held in Horsfall Bauer units with filtered air under positive pressure until trial termination. Body weights were recorded by sex and observations were made on skeletal development, feather development and the incidence of visceral lesions. Visceral tissue and bone were collected from each group for histological evaluation.

The viruses used in these studies were isolated from the intestinal tracts and visceral organs of chickens on several farms in the southeast (see Example 1).

The feed used in both trials were a broiler starter ration manufactured by the University of Georgia Poultry Science Department. A coccidiostat was not included in any of the feeds used in these trials.

Results

The most common clinical feature seen in the reproduced syndrome was very irregular feather development with many broken and poorly developed feathers. The shanks were pale and there was an increase in the incidence of perosis and other leg disorders. The most commonly observed visceral lesions were an increase in pericardial fluid with an enlargement of the proventriculus and a decrease in the size of the gizzard. In many instances there was engorgement of the glands of the proventriculus without a concurrent reduction in the size of the gizzard. Lesions in the intestinal tract consisted primarily of an increase in the size of the intestinal tract with an excessive amount of mucus and hemorrhage on the mucosal surface. The intestinal tracts were very friable and easily broken. Poorly digested feed with a characteristic orange-tinged exudate was usually found in the lower portion of the intestinal tracts.

In trial 1 there was a pronounced reduction in weight (Table 7); a similar, although less pronounced, effect was seen in trial 2 (Table 8).

TABLE 7

| | Weight in Grams | |
|---|---|---|
| Group | M | F |
| Controls | 1235[a] | 950 |
| Isolate 1 | 1028 | 786 |
| Isolate 2 | 860 | 799 |

[a]Avg. wt. for both replicates, 10 chicks per replicate.

TABLE 8

| Group | Weight in Grams | |
|---|---|---|
| | F | M |
| Control | 840[a] | 972 |
| Isolate | 826 | 932 |
| Isolate 2 | 795 | 931 |
| Isolate 3 | 793 | 879 |
| Isolate 4 | 528 | 944 |
| Isolate 5 | 834 | 924 |
| Isolate 6 | 743 | 889 |

[a]Av. wt. of 10 chicks in each group.

Gross visceral lesions were produced by both isolates in trial 1, with an enlargement of the proventriculus and an enlarged, friable intestinal tract being the most common lesions (Table 9). Similar lesions were produced by all six isolates used in trial 2 (Table 10).

TABLE 9

| | Gross Visceral Lesions | | | |
|---|---|---|---|---|
| | Heart | P.V. | Gizzard | Intestines |
| Control | 0/20 | 0/20 | 0/20 | 1/20 |
| Isolate 1 | 9/20[a] | 13/20 | 10/20 | 14/20 |
| Isolate 2 | 11/20 | 15/20 | 11/20 | 13/20 |

[a]No. with clinical lesions over the number posted.

TABLE 10

| | Gross Visceral Lesions | | | |
|---|---|---|---|---|
| | Heart | P.V. | Gizzard | Intestines |
| Control | 0/10 | 0/10 | 1/10 | 1/10 |
| Isolate 1 | 2/10[a] | 3/10 | 0/10 | 0/10 |
| Isolate 2 | 2/10 | 2/10 | 3/10 | 0/10 |
| Isolate 3 | 3/10 | 3/10 | 1/10 | 3/10 |
| Isolate 4 | 4/10 | 3/10 | 2/10 | 2/10 |
| Isolate 5 | 4/10 | 5/10 | 2/10 | 1/10 |
| Isolate 6 | 3/10 | 4/10 | 3/10 | 2/10 |

[a]No. with lesions over no. examined.

One bird in the control group was found to have a small gizzard with an enlarged, friable intestinal tract in trial 2. The incidence of perosis was much higher in trial 2 than in the first trial, with isolates four and six producing the highest incidence of perosis (Table 11).

TABLE 11

| | Gross Skeletal Lesions | |
|---|---|---|
| | Tibial dyschondroplasia | Perosis |
| Control | 3/10[a] | 1/10 |
| Isolate 1 | 4/10 | 2/10 |
| Isolate 2 | 3/10 | 1/10 |
| Isolate 3 | 1/10 | 3/10 |
| Isolate 4 | 3/10 | 3/10 |
| Isolate 5 | 3/10 | 3/10 |
| Isolate 6 | 1/10 | 7/10 |

[a]No. with lesions over no. examined.

Tibial dyshondroplasia was found in all of the groups including the controls in trial 2.

Histological lesions in the proventriculus varied from hyperplasia or hypertrophy of the glandular epithelium to fibrosis and edema. Focal areas of necrosis were occasionally seen in the proventricular glandular epithelium. Focal myocarditis, bursal atrophy and catarrhal enteritis were found in all of the injected groups.

Histological evaluation of the femur from chicks used in trial 1 indicated that animals injected with either isolate had several lesions involving the growth plate, periosteum and ossification groove. The growth plate had transverse and vertical clefts extending across the deeper portions of the proliferating and adjacent transitional zone. There was a decrease in numbers of chondrocytes along the edges of these clefts. The vertical cleft frequently separated the perichondrium from the physis. Necrosis of cartilage and fragmentation or bending of the bone bark were present at the junction of the physis with the periosteum and the periosteum was frequently hyalinized.

Similar lesions were occasionally seen in the control group. However, the lesions were much more severe and with a higher incidence in those chicks injected with isolate one.

Discussion

Proventriculitis presents a very confusing clinical picture for the diagnostician. The clinical lesions are variable and in many instances diarrhea, stunting and catarrhal enteritis are the only clinical signs presented. An enlargement of the proventriculus with a reduction in the size of the gizzard and hydropericardium were the most frequently encountered postmortem lesions seen in these trials. Chicks injected with tissue culture propagated viruses were smaller than the noninjected control chicks, exhibited an abnoraml feather development and had an increase in the incidence of lameness.

Microscopic bone lesions in the growth plate, periosteum and ossification groove are of interest because femoral head necrosis is usually much more severe in flocks with proventriculitis. The vertical clefts extending across the deeper layers of the proliferating zone and adjacent transitional zones could easily be contributing to this higher incidence of femoral head necrosis and other causes of lameness in these flocks. Vertommen et al, Avian Pathol. 9:143–152 (1980), have shown an increase in alkaline phosphatase and a decrease in the plasma carotenoid level in chicks suffering from proventriculitis.

Pigmentation of the skin and shanks is a major economical consideration in some areas of the country. Considerable effort is expended to insure a deep yellow coloration of the shanks of broilers in some companies. Pale yellow shanks were a constant clinical feature in those injected chicks used in these trials.

Decrease body weights were also observed in all of the injected groups. Elevated feed conversions and decreased body weights are a constant clinical feature in chickens with proventriculitis. Although feed conversions were not tabulated in any of these trials, there was a considerable amount of undigested feed in the fecal material in the injected groups.

EXAMPLE 3

Development of a Microneutralization Test

Using viral isolate 43A or $CO_8$, a microneutralization test has been developed to quantify antibodies against the viruses involved in the condition. The test uses constant amount of virus and the antiserum is diluted two-fold. Results obtained from the test revealed that after inoculation there is a rise in the amount of antibody present in the chickens.

EXAMPLE 4

Protective Effects of Maternal Antibody

An oil based killed vaccine was produced from the $CO_8$ strain and evaluated in broiler breeder hens. The $CO_8$ reovirus was propagated in 18–24 hr chick embryo fibroblasts. After 48 hrs post infection the cells plus media were harvested. The cells were sonicated with an ultrasonic generator at a setting of 8 for 1½ minutes (Sonifier Cell Disruptor, Model W185, Heat Systems-Ultrasonics, Inc., Plainview, L.I., NY). The virus was inactivated with 0.1% betapropiolactone for 2 hrs. After 2 hrs, 20% was blended with Marcol 52, Span 80, Tween 80, Benzyl alcohol and Triethanolamine. The virus and the other ingredients were blended for 2 to 3 minutes with a Silverson homogenizer (Silverson Machines, Ltd., Waterside, Chesham, Bucks, England). One-half ml of the vaccine was injected subcutaneously (behind the neck) into chickens between 3 and 24 weeks of age. Fifty adult Arbor Acre pullets were divided into two groups of twenty-five each and one group was vaccinated twice at four week intervals with this vaccine. Progeny from both groups were hatched and used in a challenge trial to evaluate the efficacy of this vaccine. The progeny from the vaccinated hens grew and performed as well as the non-challenged progeny. The progeny of the non-vaccinated hens were much smaller and had a higher incidence of lameness than the progeny from vaccinated hens.

EXAMPLE 5

Field Trials in Turkeys

Twenty thousand turkey hens have been vaccinated with the $CO_8$-derived vaccine. Ninety thousand poults from vaccinated hens and 90,000 poults from non-vaccinated hens have been evaluated in this study. The major criteria used in this study was the mortality occurring the first two weeks of life in these flocks. Currently the mortality in the progeny from vaccinated hens is one-half of that in the progeny from the non-vaccinated flocks.

EXAMPLE 6

Antibody Response to Experimental Vaccines

An oil-emulsion, betapropiolactone inactivated vaccine has been produced from representative isolates. Geometric mean antibody titers of breeder flocks vaccinated at 18–22 weeks of age with inactivated oil emulsion reovirus vaccine produced from the $CO_8$ strain ranged from 127.9 to 344.6; whereas, the geometric mean titers of unvaccinated breeder flocks ranged from 5.3 to 17.4 (Table 12).

TABLE 12

Geometric mean antibody titers of broiler breeder flocks vaccinated with inactivated oil emulsion vaccine prepared from the $CO_8$ strain.[A]

| Flock No. | No. Chickens | Vaccinated with Reovirus | Age of Floc Vaccination | Age of Flock | Geometric Means Antibody Titers |
|---|---|---|---|---|---|
| 1 | 8067 | Yes | 24 | 34 | 127.9 |
| 2 | 8094 | " | 24 | 34 | 344.6 |
| 3 | 8116 | " | 26 | 34 | 282.6 |
| 4 | 8316 | " | 26 | 34 | 197.4 |
| 5 | 8311 | " | 23 | 31 | 152.2 |
| 6 | 8307 | " | 23 | 31 | 231.9 |
| 7 | 8127 | " | 21 | 29 | 182.9 |
| 8 | 8097 | " | 21 | 29 | 156.0 |
| 9 | 8342 | " | 20 | 28 | 215.3 |
| 10 | 8752 | No | — | 48 | 17.4 |
| 11 | 8804 | " | — | 48 | 8.7 |
| 12 | 8410 | " | — | 46 | 12.9 |
| 13 | 8515 | " | — | 46 | 5.3 |

[A]$CO_8$ virus was used as the indicator virus in the microneutralization test.

In Table 13, it is shown that chickens vaccinated at one day of age with the oil emulsion vaccine responsed serologically to the vaccine.

TABLE 13

Geometric mean antibody titers of broiler chickens.

| Flock No. | No. Chickens | Vaccinated with Reovirus[A] | Age of Flock | Geometric Mean Antibody Titers[B] |
|---|---|---|---|---|
| 1 | 21,300 | Yes | 6 weeks | 1024 |
| 2 | 21,300 | Yes | 6 weeks | 469.5 |
| 3 | 21,300 | Yes | 5 weeks | 512 |
| 4 | 21,300 | Yes | 5 weeks | 209.1 |
| 5 | 21,300 | No | 1½ weeks | 1.5 |
| 6 | 21,300 | Yes | 1½ weeks | 24.7 |
| 7 | 21,300 | Yes | 1½ weeks | 36.2 |
| 8 | 21,300 | No | 1½ weeks | 1.5 |
| 9 | 21,300 | No | 3 weeks | 12.2 |
| 10 | 21,300 | Yes | 3 weeks | 312.2 |
| 11 | 21,300 | Yes | 3 weeks | 608.2 |
| 12 | 21,300 | No[C] | 9 days | 63.9 |
| 13 | 21,300 | No[C] | 9 days | 81.3 |
| 14 | 21,300 | No | 9 days | 14.7 |
| 15 | 21,300 | Yes | 7 weeks | 165.9 |
| 16 | 21,300 | Yes | 7 weeks | 98.7 |
| 17 | 21,300 | Yes | 7 weeks | 90.5 |
| 18 | 21,300 | No | 7 weeks | 18.4 |

[A]Inactivated, oil emulsion vaccine prepared from $CO_8$ strain. Vaccination occurred at 1 day of age.
[B]$CO_8$ strain used as indicator virus.
[C]Came from breeder flocks vaccinated with reovirus.

Seven-week-old chickens vaccinated subcutaneously at one day of age had a geometric mean titer that ranged from 90.5 to 165.9, while the unvaccinated chickens had a geometric mean titer of 18.4. Also of interest are the geometric mean titers of nine-day-old chickens (63.9 and 81.3) that were derived from breeder flocks which were vaccinated with the oil emulsion vaccine. In comparison nine-day-old unvaccinated chickens derived from breeder flocks which were not vaccinated had a geometric mean titer of 14.7.

Since it would be most economically feasible to vaccinate the breeder flocks with the inactivated oil emulsion vaccine, maternal antibody would have to protect the broiler chickens for at least 2–3 weeks. As shown in Table 14, maternal antibody titers of one-day-old chickens derived from breeder flocks vaccinated with the inactivated vaccine varied from 149.1 to 234.8; whereas, the geometric mean antibody titer of chickens from an unvaccinated breeder flock was 1.0.

TABLE 14

Geometric mean antibody titers of one-day-old chickens.

| Flock No. | No. Chickens | Breeders Vaccinated | Geometric Mean[A] Antibody Titers |
|---|---|---|---|
| 1 | 10 | Yes | 234.8 |
| 2 | 10 | Yes | 159.1 |
| 3 | 10 | Yes | 149.1 |
| 4 | 10 | No | 1.0 |

EXAMPLE 7

Field Trials in Broilers

Although laboratory trials indicate that the vaccine is effective in protecting chickens against the proventriculitis virus, results from field trials give more conclusive evidence that this vaccine is effective in preventing the syndrome. The parameters used were total condemnations, septicemia/toxemia, parts, average weights and feed conversions. Data from 1,670,508 broiler chickens vaccinated at one day of age generally had better condemnations and performance than chickens not vaccinated with the inactivated vaccines (Table 15).

in Table 15, maternal antibody did protect these chickens. The performance and condemnation were signifi-

TABLE 15

Condemnations of broiler chickens at the processing plant. Except for C farm, test flocks were vaccinated with $CO_8$ vaccine at 1 day of age.

| WK | GROWER | NO SOLD | % LIV-ABILITY | TOTAL COND (%) | AIR SAC COND (%) | SEP/TAX COND (%) | MAREK'S COND (%) | PARTS (%) | AV WT | FEED CONV |
|---|---|---|---|---|---|---|---|---|---|---|
| 1 | 1 | 60300 | 94.4 | .85 | .06 | .62 | .01 | .85 | 4.85 | 1.97 |
|  | 2 | 6050 | 94.7 | .73 | .07 | .57 | .01 | .81 | 4.63 | 1.99 |
|  | 3 | 60100 | 94.1 | 1.00 | .11 | .84 | .01 | 1.14 | 4.74 | 2.01 |
| WK AV | — | 1002250 | 95.2 | 1.06 | .13 | .82 | .01 | 1.04 | 4.59 | 2.03 |
| 2 | 1 | 40500 | 95.1 | .81 | .25 | .97 | .01 | 1.19 | 4.58 | 2.09 |
|  | 2 | 61900 | 96.9 | .74 | .12 | .61 | 0 | 1.29 | 4.32 | 2.03 |
|  | 3 | 48900 | 93.7 | .89 | .13 | .69 | 0 | 1.00 | 4.46 | 2.00 |
|  | 4 | 51400 | 92.8 | 1.15 | .25 | .85 | 0 | 1.25 | 4.44 | 2.01 |
| WK AV | — | 996113 | 95.1 | 1.15 | .18 | .86 | .01 | 1.30 | 4.48 | 2.06 |
| 3 | 1 | 19375 | 94.5 | .45 | .02 | .39 | 0 | .96 | 4.79 | 1.97 |
| WK AV | — | 941759 | 94.3 | .76 | .16 | .53 | .01 | .98 | 4.61 | 2.07 |
| 4 | 1 | 59436 | 93.0 | .63 | .33 | .29 | 0 | 1.39 | 4.77 | 2.05 |
| WK AV | — | 950694 | 94.4 | .64 | .12 | .44 | .01 | 1.45 | 4.68 | 2.07 |
| 5 | 1 | 58783 | 92.0 | .44 | .05 | .34 | 0 | .95 | 4.74 | 2.09 |
|  | 2 | 61635 | 95.3 | .89 | .33 | .49 | 0 | 1.02 | 4.72 | 2.03 |
| WK AV | — | 803803 | 94.2 | .55 | .11 | .38 | .01 | .98 | 4.71 | 2.07 |
| 6 | 1 | 58607 | 91.7 | .36 | .05 | .28 | .01 | .91 | 5.07 | 2.08 |
|  | 2 | 40593 | 95.3 | 2.24 | .05 | 1.44 | 0 | 1.18 | 4.27 | 2.03 |
|  | 3 | 59827 | 93.6 | .42 | .06 | .32 | 0 | .86 | 4.80 | 2.01 |
|  | 4 | 40054 | 94.0 | .35 | .09 | .22 | 0 | 1.00 | 4.78 | 2.05 |
| WK AV | — | 1031316 | 93.7 | .52 | .10 | .35 | .01 | 1.11 | 4.80 | 2.08 |
| 7 | 1 | 39920 | 93.7 | .94 | .37 | .56 | 0 | 1.00 | 4.57 | 2.04 |
|  | 2 | 40107 | 94.2 | .53 | .07 | .41 | 0 | .76 | 4.57 | 2.10' |
|  | 3 | 59347 | 92.9 | .58 | .06 | .47 | 0 | .87 | 4.65 | 2.04 |
|  | 4 | 59821 | 93.6 | .64 | .05 | .23 | 0 | .72 | 4.83 | 2.05 |
| WK AV | — | 1013531 | 94.3 | .75 | .13 | .54 | .01 | .94 | 4.54 | 2.08 |
| 8 | 1 | 58943 | 92.2 | .64 | .04 | .54 | 0 | .75 | 4.72 | 1.976 |
|  | 2 | 59960 | 93.8 | .45 | .05 | .36 | 0 | .83 | 4.45 | 2.04 |
|  | 3 | 38303 | 89.9 | .74 | .15 | .51 | 0 | .91 | 4.54 | 1.99 |
|  | 4 | 47925 | 93.6 | .86 | .24 | .75 | 0 | .95 | 4.36 | 2.10 |
| WK AV | — | 936020 | 93.1 | .73 | .17 | .57 | .01 | .91 | 4.46 | 2.05 |
| 9 | 1 | 52300 | 95.4 | .49 | .13 | .31 | 0 | .71 | 4.85 | 2.09 |
|  | 2 | 59158 | 92.6 | .22 | .04 | .14 | 0 | .56 | 4.60 | 2.11 |
|  | 3 | 63158 | 92.3 | .36 | .07 | .25 | 0 | .90 | 4.58 | 2.06 |
| WK AV | — | 805922 | 94.3 | .57 | .13 | .35 | .03 | .87 | 4.44 | 2.08 |
| 10 | 1 | 43602 | 92.8 | .46 | .11 | .29 | 0 | .85 | 4.69 | 2.04 |
|  | 2 | 48169 | 94.1 | .42 | .07 | .26 | 0 | .96 | 4.64 | 2.04 |
|  | 3 | 58365 | 91.3 | .90 | .07 | .57 | 0 | .87 | 4.29 | 2.04 |
|  | 4 | 58284 | 91.2 | .42 | .10 | .25 | 0 | .62 | 4.67 | 2.06 |
| WK AV | — | 870625 | 93.1 | .53 | .14 | .32 | .01 | .86 | 4.54 | 2.06 |
| 11 | 1 | 59559 | 93.2 | .30 | .24 | 0 | 0 | .93 | 4.74 | 2.08 |
|  | 2 | 38677 | 90.8 | .84 | .43 | .35 | 0 | 1.23 | 4.63 | 2.06 |
| WK AV | — | 977077 | 94.1 | .64 | .25 | .39 | .01 | .97 | 4.51 | 2.08 |
| 12 | 1(C farm)[d] | 59709 | 94.1 | .49 | .13 | .22 | 0 | .75 | 4.82 | 2.03 |
|  | 2(C farm)[d] | 58603 | 95.2 | .51 | 10 | .31 | 0 | .63 | 4.91 | 2.08 |
|  | 3(C farm)[d] | 48433 | 95.4 | .39 | .09 | .22 | .01 | .84 | 4.73 | 2.05 |
|  | 4(C farm)[d] | 59903 | 95.1 | .60 | .11 | .41 | 0 | .79 | 4.69 | 2.07 |
| WK AV | — | 964331 | 94.2 | .84 | .14 | .57 | .02 | 1.13 | 4.70 | 2.10 |

[d]Not vaccinated, but were progeny of vaccinated breeder flocks.

The unvaccinated birds were listed as the week's average or the total number of chickens processed that week. This figure does not include the vaccinated chickens. Also, the 226,642 broiler chickens designated as "C farm" chickens were progeny from breeder flocks that were vaccinated with the inactivated vaccine. However, the progeny were not vaccinated. As shown in Table 15, maternal antibody did protect these chickens. The performance and condemnation were significantly better than in the unvaccinated chickens. Also, it should be pointed out that during the "grow-out" period there were many more culls in flocks of chickens that are not vaccinated and do not come from vaccinated parent flocks when compared to progeny that are derived from vaccinated breeder flocks (Table 16).

TABLE 16

Comparison of mortality and cull chickens in broiler flocks derived from either vaccinated or unvaccinated breeder flocks.

| GROWER NO. | VACCINATED PARENT FLOCK | NO. OF BROILERS | AGE OF BROILERS | MORTALITY | CULLS |
|---|---|---|---|---|---|
| 1 | No | 21,300 | 6 | 207 | 569 |
|  | No | 21,300 | 6 | 231 | 480 |
|  | No | 21,300 | 6 | 267 | 565 |
| 2 | Yes | 21,300 | 6 | 213 | 105 |
|  | Yes | 21,300 | 6 | 243 | 163 |
|  | Yes | 21,300 | 6 | 271 | 109 |
| 3 | No | 21,300 | 6 | 257 | 225 |

TABLE 16-continued

Comparison of mortality and cull chickens in broiler flocks derived from either vaccinated or unvaccinated breeder flocks.

| GROWER NO. | VACCINATED PARENT FLOCK | NO. OF BROILERS | AGE OF BROILERS | MORTALITY | CULLS |
|---|---|---|---|---|---|
|  | Yes | 21,300 | 6 | 230 | 115 |

EXAMPLE 8

Laboratory Vaccination Trials

The results shown in Tables 17-21 indicated that in laboratory trials the $CO_8$ virus is the best candidate for a vaccine when compared to the 81-5, 1133(VA) and 172 isolates. These broiler chickens were vaccinated at 1 day of age with inactivated oil emulsion reovirus vaccine and were challenged intramuscularly or orally at 18 days with either the 81-5 or 172 reovirus isolate. Regardless of the method of challenge or the challenge virus used, the $CO_8$ vaccine proved to be the most effective. As shown in Table 17 there was weight depression in the control chickens when compared to the vaccinated chickens. Although there were lesions in the chickens vaccinated with 81-5, 1133(VA) and 172, the lesions were not as severe in the vaccinated chickens as in the controls. The weight depression was not as dramatic in the chickens challened orally with the 81-5 isolate. In order to determine the immunosuppressive effects of the proventriculitis virus the chickens in Tables 17-21 were vaccinated at 25 days with Newcastle disease virus vaccine. Although there was probably some immunosuppression in some of the groups, it was not significant. More time should have elapsed between challenging the birds with the reovirus and the vaccination of the chickens with the Newcastle disease vaccine.

TABLE 17

Weights and lesions after vaccination of one-day-old chickens with reovirus oil emulsion vaccine and intramuscular challenge at 18 days of age with the 81-5 isolate.

| Vaccine | Weights (Lbs) Days Post Challenge | | No. +/No. Started |
|---|---|---|---|
|  | 11 | 26 |  |
| $CO_8$ | 2.46 | 3.96 | 1/15 |
| 81-5 | 2.43 | 3.86 | 13/15 |
| 1133(VA) | 2.45 | 3.865 | 13/16 |
| 172 | 2.40 | 3.71 | 14/14 |
| CONTROL | 2.50 | 3.69 | 14/14 |

TABLE 18

Weights and lesions after vaccination of one-day-old chickens with the reovirus oil emulsion vaccine and oral challenge at 18 days of age with the 81-5 isolate.

| Vaccine | Weights (Lbs) Days Post Challenge | | No. +/No. Started |
|---|---|---|---|
|  | 11 | 26 |  |
| $CO_8$ | 2.45 | 3.74 | 3/16 |
| 81-5 | 2.43 | 3.84 | 13/14 |
| 1133(VA) | 2.33 | 3.71 | 13/15 |
| 172 | 2.24 | 3.63 | 10/15 |
| CONTROL | 2.33 | 3.65 | 10/15 |

TABLE 19

Weights and lesions after vaccination of one-day-old chickens with reovirus oil emulsion vaccines and intramuscular challenge at 18 days of age with the 172 isolate.

| Vaccine | Weights (Lbs) Days Post Challenge | | No. +/No. Started |
|---|---|---|---|
|  | 11 | 26 |  |
| $CO_8$ | 2.25 | 3.89 | 3/16 |
| 81-5 | 2.36 | 3.76 | 10/16 |
| 1133(VA) | 2.32 | 3.80 | 13/16 |
| 172 | 2.31 | 3.78 | 11/15 |
| CONTROL | 2.28 | 3.78 | 10/13 |

TABLE 20

Weights and lesions after vaccination of one-day-old chickens with reovirus oil emulsion vaccines and oral challenge at 18 days with the 172 isolates.

| Vaccine | Weights (Lbs) Days Post Challenge | | No. +/No. Started |
|---|---|---|---|
|  | 11 | 26 |  |
| $CO_8$ | 2.24 | 3.76 | 3/15 |
| 81-5 | 2.40 | 3.77 | 9/12 |
| 1133(VA) | 2.38 | 4.02 | 9/15 |
| 172 | 2.28 | 3.83 | 7/15 |
| CONTROL | 2.40 | 3.88 | 11/15 |

TABLE 21

Weights and lesions after vaccination of one-day-old chickens with reovirus vaccine.

| Vaccine | Weights (lbs) Days Post Challenge | | No. +/No. Started |
|---|---|---|---|
|  | 11 | 26 |  |
| $CO_8$ | 2.39 | 3.70 | 2/15 |
| 81-5 | 2.48 | 3.52 | 2/10 |
| 1133(VA) | 2.57 | 3.55 | 1/13 |
| 172 | 2.47 | 3.49 | 1/13 |
| CONTROL | 2.48 | 3.51 | 2/13 |

Results from Table 22 clearly demonstrate that the $CO_8$ isolate is superior to the 81-5, 1133(VA) and 172 isolates as candidates for a vaccine. The $CO_8$ vaccinated chickens were protected when challenged with either the 81-5, 1133(VA) or 172 isolates. Chickens vaccinated with the other isolates (172, 1133, 81-5) were protected when challenged with its homologous challenge virus but none were as effective as the $CO_8$ vaccine.

TABLE 22

Gross lesions after vaccination of one-day-old chickens with reovirus vaccines and intramuscular challenge at 18 days of age.

| Vaccine | challenge virus | | | | | |
|---|---|---|---|---|---|---|
|  | $CO_8$ | 81-5 | 1133(VA) | 172 | CON | CON |
| $CO_8$ | $1/8^{A,B}$ | 1/8 | 0/8 | 0/7 |  |  |
| 81-5 | 5-8 | 2/8 | 4/8 | 2/7 |  |  |
| 1133 (VA) | 2/8 | 7/8 | 2/8 | 2/5 |  |  |
| 172 | 2/8 | 6/8 | 3/8 | 0/5 |  |  |
| Control | 7/8 | 6/8 | 8/8 | 7/8 |  |  |

TABLE 22-continued

Gross lesions after vaccination of one-day-old chickens with reovirus vaccines and intramuscular challenge at 18 days of age.

| Vaccine | CO$_8$ | 81-5 | 1133(VA) | 172 | CON | CON |
|---|---|---|---|---|---|---|
| Control | — | — | — | — | 0/6 | 0/3 |

$^A$No. + No. Started
$^B$Not including early mortality

The CO$_8$ isolate was deposited at the ATCC on July 7, 1982, with ATCC No. VR2040.

Having now fully described this invention it will be apparent to those of ordinary skill in the art that the same can be performed within a wide and equivalent range of parameters, conditions, compositions, modes of administration, isolates, avian species, and the like, without affecting the spirit or scope of the invention or of any embodiment thereof.

What is claimed as new and desired to be secured by Letters Patent of the United States is:

1. A vaccine capable of protecting poultry against proventriculitis, which comprises:
    an antigenic material capable of inducing in said poultry an immune response against avian proventriculitis reovirus, wherein said antigenic material is selected from the group consisting of live, attenuated, and inactivated proventriculitis reovirus and immunologically active subcomponents thereof, wherein said reovirus has the identifying characteristics of ATCC No. VR2040 or a progeny thereof, and
    a pharmacologically acceptable carrier.
2. The vaccine of claim 1 wherein said carrier is a biocompatible oil.
3. The vaccine of claim 1 wherein said reovirus is inactivated with propiolactone.
4. The vaccine of claim 1 wherein said reovirus is attenuated by serial passage.
5. The vaccine of claim 1 in unit dosage form.
6. A method of protecting a poultry animal against proventriculitis which comprises:
    vaccinating said poultry animal with the avian proventriculitis vaccine of claim 1, in an amount sufficient to produce an immune response against proventriculitis reovirus in said animal.
7. The method of claim 6 wherein said vaccine comprises antigenic material selected from the group consisting of live, attenuated and inactivated proventriculitis reovirus.
8. The method of claim 6 wherein said carrier is a biocompatible oil.
9. The method of claim 7 wherein said reovirus is inactivated with propiolactone.
10. The method of claim 7 wherein said reovirus is attenuated by serial passage.
11. The method of claim 6 wherein said poultry animal is a reproductive hen.
12. Avian proventriculitis reovirus having the identifying characteristics of ATCC No. VR2040 or a progeny thereof.

* * * * *